United States Patent [19]

Young et al.

[11] Patent Number: 5,038,765
[45] Date of Patent: Aug. 13, 1991

[54] ORTHOPAEDIC BIPIVOTAL HINGE AND PIVOT CONTROL SYSTEM THEREFOR

[75] Inventors: David E. Young, Watlington; Kenneth P. Davis, High Wycombe, both of England

[73] Assignee: Protectair Limited, Abingdon, England

[21] Appl. No.: 548,611

[22] Filed: Jul. 5, 1990

[30] Foreign Application Priority Data

Aug. 14, 1989 [GB] United Kingdom ............... 8918523
Aug. 25, 1989 [GB] United Kingdom ............... 8919401

[51] Int. Cl.$^5$ .......................... A61F 5/04; A61F 5/00
[52] U.S. Cl. .................................. 128/88; 128/80 F
[58] Field of Search ............ 128/88, 80 R, 80 A, 128/80 C, 80 F, 80 G, 80 J, 87 R

[56] References Cited

U.S. PATENT DOCUMENTS

| | | | |
|---|---|---|---|
| 3,187,347 | 6/1965 | Terron | 128/88 |
| 3,902,482 | 9/1975 | Taylor | 128/88 |
| 4,323,059 | 4/1982 | Rambert | 128/88 |
| 4,520,802 | 6/1985 | Mercer | 128/88 |
| 4,524,764 | 6/1985 | Miller | 128/88 |
| 4,554,913 | 11/1985 | Womack | 128/88 |
| 4,556,053 | 12/1985 | Irons | 128/88 |
| 4,573,455 | 3/1986 | Hoy | 128/88 |
| 4,633,867 | 1/1987 | Kausek | 128/88 |
| 4,732,143 | 3/1988 | Kausek | 128/88 |

FOREIGN PATENT DOCUMENTS

| | | |
|---|---|---|
| 1008446 | 5/1957 | Fed. Rep. of Germany . |
| 3535578 | 5/1986 | Fed. Rep. of Germany . |
| 2182714 | 2/1987 | United Kingdom . |
| 2208065 | 2/1989 | United Kingdom . |

Primary Examiner—Robert A. Hafer
Assistant Examiner—Michael Brown
Attorney, Agent, or Firm—Tilton, Fallon, Lungmus

[57] ABSTRACT

A true bipivotal hinge for orthopaedic use having a hinge body and a pair of hinge arms with adjacent end portions pivotally connected to the side walls of the body for independent pivotal movement of each arm. A T-shaped insert element is removably secured within the hinge body and has a pair of stop portions with abutment surfaces engagable with the end portions of the arms for limiting the degree of extension of such arms. In a system for accommodating such a hinge to a patient's needs, a plurality of insert elements are provided, each being of substantially the same size and shape but having distinctive angularity of their abutment surfaces so that by interchanging one insert element for another, the hinge may be adjusted to provide the required degree of maximum arm extension.

10 Claims, 1 Drawing Sheet

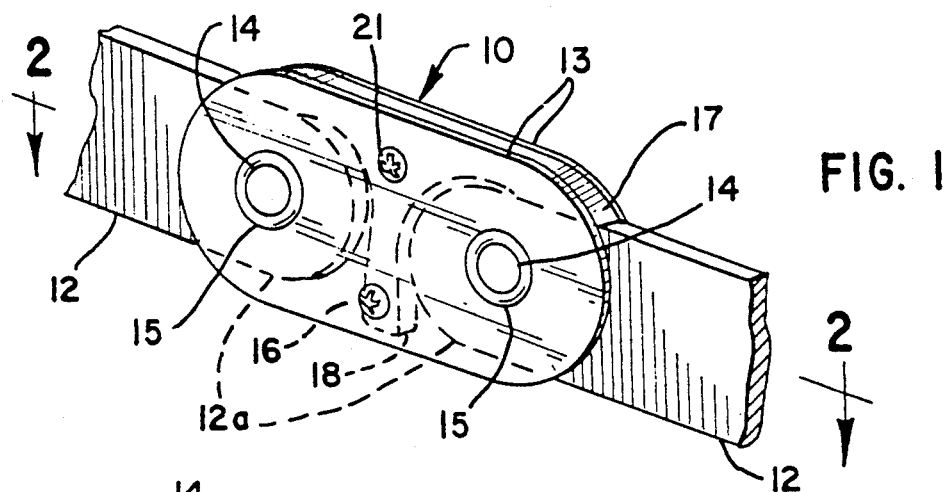
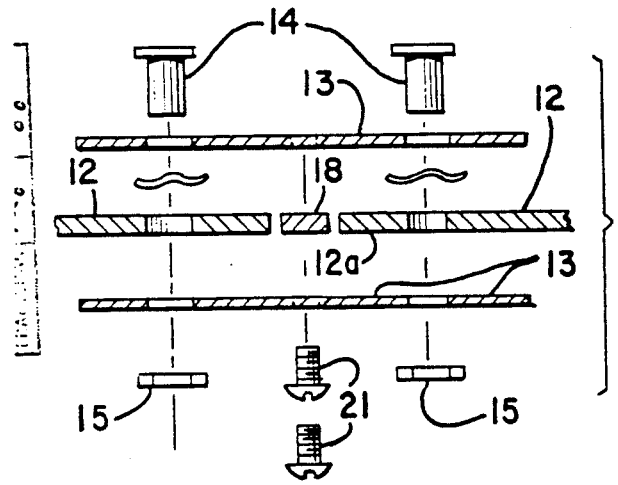
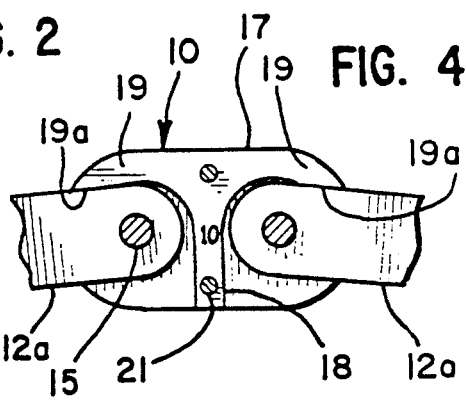
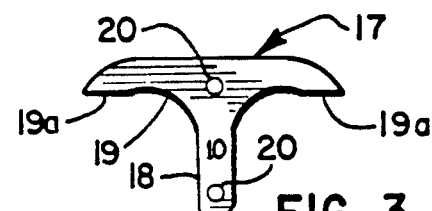
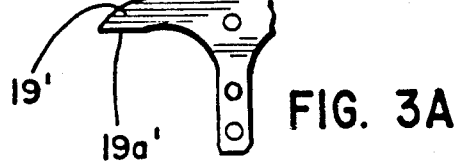
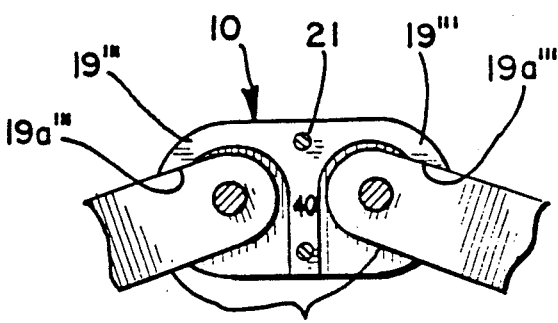
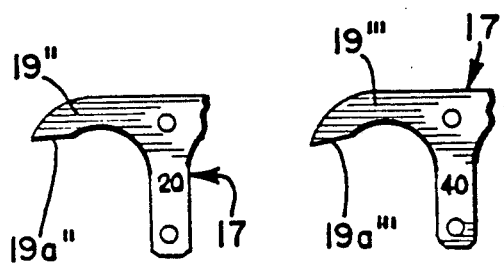

ORTHOPAEDIC BIPIVOTAL HINGE AND PIVOT CONTROL SYSTEM THEREFOR

BACKGROUND AND SUMMARY

There are many hinge designs used in orthopaedic splints and braces, most of them having either a single pivot or two pivots supporting arms which are geared together. Bipivotal hinges in which the arms are not geared together but are truly independently pivotal about their respective axes have become increasingly popular in recent years with the realization that such a construction is superior to the others in providing the freedom necessary to accommodate the complex and changing locus of the axis of the knee during the full flexion/extension cycle.

We have developed a number of adjustment mechanisms for true bipivotal hinges, all of them providing continuously variable stops, and these are described in GB 2,182,714, published UK application 2,208,065A, and in European patent publication 0,109,847. However, the degree of sophistication disclosed therein may add substantially to cost and is not always required.

Two geared polycentric hinges are known to us in which insert elements may be added to effectively jam the gears and limit the extent of pivotal movement. One such geared hinge is used in a brace by Donjoy Inc. of Carlsbad, Calif., U.S.A. and the other is a plastic hinge made by Otto Bock of Duderstadt, West Germany.

Accordingly, an important aspect of this invention lies in providing a true bipivotal hinge in which the hinge arms may pivot independently in relation to each other and to a hinge body and in which a simple but highly effective system is provided for altering the hinge so that the extent of pivotal movement of the arms is selectively controlled. In such a system, a plurality of insert elements are provided, each insert element being capable of being readily attached to or removed from the hinge body for controlling the extent of pivotal movement of the respective hinge arms. Since the insert elements are constructed to limit pivotal movement at different selected angles, such insert elements may be interchanged so that any given hinge mechanism is tailored to the needs of a patient. As those needs change, the insert elements may be changed accordingly. Conversely, if the same brace is to be re-used with a different patient, the limits of pivotal movement may be easily modified by simply interchanging the insert element to meet the needs of the second patient.

Briefly, the bipivotal hinge system takes the form of a hinge body having a pair of side walls defining a space therebetween. Two hinge arms have adjacent end portions located in that space, the arms being pivotally connected to the side walls for independent flexion/extension with respect to the other arm. A plurality of insert elements are provided, each having a mounting portion and two integral stop portions. The mounting portions of all of the insert elements are of substantially the same size and shape but the stop portions of the respective elements are of different size and shape. Since the stop portions of the different insert elements are engagable with the arms at different angles of pivot for each of the plurality of insert elements, the extent of independent pivotal movement of the hinge arms may be selectively controlled simply by interchanging the insert elements in the hinge body. Connecting means are provided for removably securing any one of the insert elements in the hinge body with the stop portions thereof positioned for engagement with the adjacent end portions of the hinge arms for limiting the extent of independent pivotal movement of each of those arms.

In a preferred embodiment, each insert element is of generally T-shaped configuration, having a central stem that constitutes the mounting portion of the element and a pair of outwardly-projecting top members that constitute the stop portions of the element. The top members project outwardly in opposite directions with each top member having an abutment surface for engagement with one of the hinge arms. The angles of the abutment surfaces differ from one insert element to the next and may even, if desired, differ for the two abutment surfaces of a single insert element.

Other features, advantages, and objects of the invention will be apparent from the specification and drawings.

DRAWINGS

FIG. 1 is a general perspective view of an orthopaedic hinge embodying the present invention.

FIG. 2 is an exploded sectional view taken along line 2—2 of FIG. 1 (unexploded).

FIG. 3 is a side elevational view of a stop element for limiting the extent of anterior pivotal movement of the hinge arms at 10 degrees of flexion.

FIGS. 3A–3C are fragmentary elevational views showing insert elements similar to the one depicted in FIG. 3 but having stop portions for limiting anterior pivotal movement of hinge arms at zero degrees, 20 degrees, and 40 degrees of flexion.

FIG. 4 is a sectional view showing the relationship between a 10 degree insert element and the other functional elements of the hinge mechanism.

FIG. 5 is a sectional view similar to FIG. 4 but showing the cooperative relationship involving 40 degree insert element.

DETAILED DESCRIPTION OF PREFERRED EMBODIMENT

Referring to the drawings, the numeral 10 designates an orthopaedic bipivotal hinge having a hinge body and a pair of hinge arms 12. The hinge body consists essentially of two side walls or plates 13 that are connected by rivets 14 and washers 15. The side walls are planar and parallel, defining a space 16 therebetween for receiving the adjacent end portions 12a of hinge arms 12.

Insert element 17 is generally T-shaped in configuration, as shown most clearly in FIGS. 3 and 1. In a complete system, a plurality of such insert elements are provided, each differing from the other in slight but highly significant respects. Each insert element 17 includes a mounting portion 18, which constitutes the stem of the "T", and a pair of stop portions 19 which are the oppositely-directed outwardly-projecting top arms or members of the "T". The mounting portions 18 of all of the insert elements of the group are substantially identical in shape and size. Each such stem portion has a pair of upper and lower openings 20 for receiving mounting screws 21 that extend through both walls 13 of the hinge body. As shown most clearly in FIGS. 1 and 4, the mounting portion 18 extends between the adjacent ends of the hinge arms and is spaced from such arms to avoid any interference with pivotal movement of those arms.

The stop portions 19 of each insert element are distinctively different from those of other insert elements of the group. Referring again to FIG. 3, it will be observed that each stop portion 19 has an abutment surface 19a positioned for engagement with the anterior surface of a hinge arm 12 to limit the extension or anterior pivotal movement of that arm. The particular insert element depicted in FIGS. 3 and 4 has abutment surfaces 19a arranged at an angle of 10 degrees with respect to each other (or 5 degrees each in relation to a line passing through both pivot axes of the bipivotal hinge). Therefore, the two hinge arms 12, when extended into contact with stop portions 19, will be blocked against being extended into positions closer than 10 degrees from full (180 degree) extension.

Insert element 17 shown in FIG. 3A is identical except that stop portions 19' have their abutment surfaces 19a' disposed in zero degrees deflection from full extension, that is, the abutment surfaces 19a' lie in the same plane. The insert element 17 of FIG. 3B differs only to the extent that stop portions 19" have abutment surfaces 19a" disposed at a deflection of 20 degrees from full (180 degree) extension. Similarly, insert element 17 of FIG. 3C is identical except that its abutment surfaces 19a'" of stop portions 19'" are disposed at a deflection of 40 degrees from full (180 degree) extension. Therefore, as shown in FIG. 5, if a hinge assembly is fitted with the insert element of FIG. 3C, the stop portions 19'" will prevent hinge arms 12 from approaching closer than 40 degrees from full 180 degree extension.

As already indicated, the deflection from full extension for the insert elements of FIGS. 3, 3B, and 3C is shared equally by the angular abutment surfaces of the two stop portions. For example, abutment surfaces 19a'" are each disposed at angles of 20 degrees short of full extension, resulting in a combined or total deviation of 40 degrees. It is to be understood, however, that in each case the insert elements may be constructed so that the angular deviation is not shared equally. Thus, in the case of a 40 degree insert element, one abutment surface may be disposed at less than 20 degrees and the other at more than 20 degrees, yielding a total of 40 degrees.

It will be observed that the stop portions of all of the insert elements have a span that is substantially greater than the distance between the two pivot axes of the bipivotal hinge assembly, thereby providing substantial mechanical advantage in blocking extension of the hinge arms at the limits provided by the respective inserts. The insert elements may be formed of steel or any other suitable material capable of withstanding the forces generated in use of the device. Should the insert element be formed of a material capable of limited flexure, it will be observed that slight flexure of stop portions 19-19'" at maximum extension of the arms 12 would be possible because the only attachment between each insert element and the side walls 13 of the hinge body is at connectors 21 disposed along the midline of mounting portion 18.

While in the foregoing we have disclosed embodiments of the invention in considerable detail for purposes of illustration, it will be understood by those skilled in the art that many of such details may be varied without departing from the spirit and scope of the invention.

We claim:

1. An orthopaedic bipivotal hinge system comprising a hinge body having a pair of side walls defining a space therebetween; two hinge arms having adjacent end portions located in said space and independently pivotally connected to said side walls for pivotal movement of each arm independently of the other of said arms; and a plurality of generally T-shaped insert elements each having a central stem portion and two integral stop portions extending outwardly from said stem portion at one end thereof; said insert elements each being dimensioned to be received in said space between said side walls; ;said stem portions of all of said insert elements being of substantially the same size and shape and being receivable in said space between said end portions of said hinge arms; said stop portions of each insert element being of different shape than the stop portions of other of said insert elements; and connecting means for removably securing any one of said insert elements to said side walls in a predetermined location in said space with the stop portions thereof positioned for engagement with said adjacent end portions of said arms for limiting the extent of independent pivotal movement of each hinge arm; said stop portions of different insert elements being engagable with said arms at different angles of pivot of said arms, whereby, the extent of independent pivotal movement of said arms is selectively controllable by interchanging said insert elements in said hinge body.

2. The system of claim 1 in which said stem portion of each insert element has two openings therein; said connecting means comprising screw elements securable to said side walls and extending through said openings for releasably securing each insert element within said space.

3. The system of claim 1 in which each of said step portions has an abutment surface for engagement with one of said hinge arms.

4. The system of claim 3 in which said abutment surfaces are on the undersides of said stop portions.

5. The system of claim 1 in which said stop portions limit pivotal movement of said hinge arms in directions of extension.

6. An orthopaedic bipivotal hinge comprising a hinge body having a pair of side walls defining a space therebetween; two hinge arms having adjacent end portions located in said space and independently pivotally connected to said side walls for pivotal movement of each arm in directions of extension and flexion independently on the other of said arms; ;and a T-shaped insert element removably secured between said side walls having a central stem portion and two integral stop portions extending outwardly from said stem portion at one end thereof; said stop portions having abutment surfaces engagable with said hinge arms for limiting the extent of independent pivotal movement of such arms; said stem portion being generally coplanar with said hinge arms and extending therebetween; and connecting means removably securing said stem portion to both of said side walls.

7. The hinge of claim 6 in which said stem has two openings therein; said connecting means comprising screw elements securable to said side walls and extending through said openings for releasably securing said insert element within said space.

8. The hinge of claim 6 in which said abutment surfaces are each disposed at a selected angle within the range of zero degrees to 20 degrees measured from a line passing through the two pivot axes of said bipivotal hinge.

9. The hinge of claim 8 in which said two abutment surfaces are at the same angle relative to said line.

10. The hinge of claim 8 in which said two abutment surfaces are at different angles in relation to said line.

* * * * *